(12) United States Patent
Dong (10) Patent No.: US 6,406,911 B1
(45) Date of Patent: Jun. 18, 2002

(54) COMPOSITIONS AND METHODS FOR SENSITIVE DETECTION OF HIV INFECTION AND MONITORING OF DRUG RESISTANCE

(75) Inventor: Jian-yung Dong, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 09/314,259

(22) Filed: May 18, 1999

Related U.S. Application Data
(60) Provisional application No. 60/117,136, filed on Jan. 25, 1999.

(51) Int. Cl.$^7$ .............................................. C12N 15/63
(52) U.S. Cl. .............................. 435/455; 435/5; 435/6; 435/69.1; 435/69.2; 435/70.1; 435/173.4; 435/325; 435/339.1; 435/320.1; 435/475; 435/476; 536/23.1; 536/23.4; 536/23.72
(58) Field of Search .............................. 435/5, 6, 8, 14, 435/18, 69.1, 69.2, 69.7, 69.8, 70.1, 173.4, 235.1, 325, 339.1, 320.1, 455; 536/23.1, 23.4, 23.72, 24.1

(56) References Cited

U.S. PATENT DOCUMENTS 5,837,464 A  11/1998  Capon et al. .................. 435/6

FOREIGN PATENT DOCUMENTS

GB  2 224 712 A  12/1991  ............ C12N/15/79
WO  WO 93/05185  3/1993  ............ C12Q/1/70

OTHER PUBLICATIONS

Harrington et al. Cofactor requirement for human immunodeficiency virus type 1 entry into a CD4–expressing human cell line. Journal of Virology (1993) vol. 67, No. 10, pp. 5939–5947.*
Kimpton et al. Detection of replication–competent and pseudotyped human immunodeficieny virus with a sensitive cell line on the basis of activation of an integrated beta–galactocidase gene. Journal of Virology (1992) vol. 66, No. 4, pp. 2232–2239.*
Vodicka et al. Indicator cell lines for detection of primary strains of human and simian immunodeficiency viruses. Virology. vol. 233 (1997) pp. 193–198.*
Deng et al. Identification of a major co–receptor for primary isolates of HIV–1. Nature. vol 381 (1996) pp. 661–666.*
Alberts et al. Eds., 3rth Ed. Garland Publishing Inc., New York & London, "Molecular Biology of the Cell"p. 160–162(1994).
Andrea G. Bodnar et al., "Extension of Life–Span By Introduction of Telomerase Into Normal Human Cells" www.sciencemag.org, vol 279, Jan. 16, 1998, pp. 349–352.

D.S. Mimitrov et al., "Topical Review—HIV Coreceptors," The Journal of Membrane Biologg, Jun. 1, 1998, pp. 75–90.
Edward A. Berger, "HIV Entry and Tropism" Mechanisms of Lymphocyte Activation and Immune Regluation VII, 1998, pp. 151–157.
Lee, A.H. et al., "Generation of the Replication–Competent Human Immunodeficiency Virus Type 1 Which Expresses A Jellyfish Green Fluorescent Protein", Biochemical and Biophysical Research Communications, 233, pp. 288–292 (1997).
Gervaix, A. et al., "A New Reporter Cell Line To Monitor HIV Infection and Drug Susceptibility In Vitro", Proc. Natl. Acad. Sci. USA, vol. 94, pp.4653–4658, Apr. 1997.
Koseki, S. et al. "A Simple Assay System For Examination of the Inhibitory Potential In Vivo of Decoy RNA's Ribozymes and Other Drugs By Measuring The Tat–Mediated Transcription Of A Fusion Gene Composed of the Long Termianl Repeat of HIV–1 and A Gene For Luciferase", Journal of Controlled Release, 53 (1998) pp. 159–173.
Jamieson, B.D. et al., "In Vivo Pathogenesis of a Human Immunodeficiency Virus Type 1 Reporter Virus", Journal of Virology, Aug. 1998, pp. 6520–6526.
Dorsky, D.I. et al., "Detection of HIV–1 Infection With Green Fuorescent Protein Reporter System", Journal of Acquired Immune Deficiency Syndromes, 13, pp. 308–313, (1996).

* cited by examiner

Primary Examiner—Jeffrey Stucker
Assistant Examiner—Ulrike Winkler
(74) Attorney, Agent, or Firm—David J. Weitz; Shirley Chen; Wilson Sonsini Goodrich & Rosati (57) ABSTRACT

A method is provided for detecting a presence of HIV virus in a sample comprising: taking a culture of recombinant cells which (a) are capable of cell division, (b) express CD4 receptor and one or more additional cell surface receptors necessary to allow the HIV virus to infect, (c) enable the HIV virus to replicate and infect the noninfected cells in the cell culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus; contacting the cell culture with a sample to be analyzed for the presence of HIV virus in the sample; and detecting a change in a level of expression of the reporter gene in cells in the recombinant cell culture. The method can be used to detect the presence of HIV virus in a sample, detect the presence of different strains of HIV virus in a sample, detect HIV drug resistance in a sample, determine what combination of one or more anti-HIV agents would be effective in treating a patient, and screen compositions for anti-HIV activity.

24 Claims, 3 Drawing Sheets

COMPOSITIONS AND METHODS FOR SENSITIVE DETECTION OF HIV INFECTION AND MONITORING OF DRUG RESISTANCE

RELATIONSHIP TO COPENDING APPLICATIONS

This application claims priority to "METHODS OF MONITORING HIV DRUG RESISTANCE," Provisional Application Ser. No.: 60/117,136; Filed: Jan. 25, 1999 which is incorporated herein by reference.

BACKGROUND OF THE INVENTION

1. Field of the Invention

The present invention relates to recombinant cell lines and methods for detecting and monitoring viral infection. More particularly, the invention relates to recombinant cell lines and methods for detecting HIV infection, monitoring HIV for drug resistance and screening for anti-HIV agents.

2. Description of Related Art

Human immunodeficiency virus (HIV) has been implicated as the primary cause of the slowly degenerate disease of the immune system termed acquired immune deficiency syndrome (AIDS). Infection of the $CD4^+$ subclass of T-lymphocytes with the HIV type-1 virus (HIV-1) leads to depletion of this essential lymphocyte subclass which inevitably leads to opportunistic infections, neurological disease, neoplastic growth and eventual death.

Infection with human immunodeficiency virus (HIV) is a chronic process with persistent, high rates of viral replication. The pathogenesis of HIV-1 infection is characterized by a variable but often prolonged asymptomic period following the acute viremic phase. Previous work has established a correlation between HIV disease progression and increasing amounts of infectious virus, viral antigens, and virus-specific nucleic acids (Ho et al., New England. J. Med. 321: 1621–1625 (1989); Schnittman et al. AIDS Res. Hum. Retroviruses 7: 361–367 (1991); Pantalco et al. Nature 362: 355–358 (1993)).

A variety of reagents and assays have been developed to detect the infection of HIV and monitor the progression of HIV in the body. For example, counting the depletion of $CD4^+$ cells has been used to indicate the prognosis of AIDS. Serological screening techniques are also being utilized worldwide for the detection of HIV, where the presence of the antibody against HIV antigens, such as the HIV p24 antigen, is detected.

An ELISA assay is currently being utilized on serum samples in most hospitals and screening laboratories to make the determination. However, currently used ELISA assays may not be sensitive enough to detect all HIV infected individuals. This is because that some HIV infected individuals do not have detectable levels of serum antibody to HIV. There may be a significant time lag between detection of HIV infection and seroconversion. In addition, some HIV infected but seronegative individuals might never convert but will remain infected throughout theirs lives. Thus, such a screening method may generate false negatives, which in turn may increases the probability of HIV infection of healthy people by these individuals.

Another method for detecting HIV infection in seronegative individuals was described (Jehuda-Cohen, T. et al. Proc. Natl. Acad. Sci. UAS, 87: 3972–3076 (1990)) wherein peripheral blood mononuclear cells (PBMC) are isolated from the blood and then exposed to a mitogen such as pokeweed mitogen. Incubation of isolated PBMC with pokeweed mitogen caused the PBMC to secret immunoglobulins that were specific for HIV. The failure of the ELISA assay to detect all HIV infected individuals places the population at risk by misleading the HIV infected individuals that they are not infected, thereby making it more likely that the HIV infected individuals will unknowingly infect others.

The existence of HIV has also been determined by using the reverse transcriptase-polymerase chain reaction (RT-PCR) to amplify plasma HIV RNAs (U.S. Pat. No. 5,674,680). This method is used to detect three types of HIV mRNA in peripheral blood cells: unspliced, multiple spliced, and single-spliced mRNA in AIDS patients, HIV-infected but asymptomatic individuals and individuals who are undergoing therapy for AIDS. However, the correlation between the differences in HIV mRNA levels and AIDS prognosis needs to be established.

Many antiviral drugs have been developed to inhibit HIV infection and replication by targeting HIV reverse transcriptase and proteases. Treatment following a prolonged single drug regimen has met with limited success where there is relatively small drop in viral load, followed by a rise in amount of detectable virus in blood, presumably due to the development of drug resistance strains of HIV. The resistance of HIV to drugs is not only associated with the high mutation rates of HIV but also due to the selective pressure of prolonged anti-HIV drug therapy. Since the original description of diminished susceptibility of isolates of HIV-1 to zidovudine (AZT) (Larder et al. Science (1989) 243:1731–1734), the literature has disclosed many descriptions of diminished susceptibility to AZT in different clinical situations, with different assay systems, and of genetic mutations responsible for changes in susceptibility. For example, isolates from subjects not treated with AZT display a narrow range of susceptibilities to AZT, with the 50% inhibitory concentrations (IC50) ranging from 0.001 to 0.04 $\mu M$ (Larder et al. (1989), supra; Rooke et al. AIDS (1989) 3:411–415; Land et al. J Infect Dis (1990) 161:326–329; Richman et al. J. AIDS (1990) 3:743–746; Tudor-Williams et al. Lancet (1992) 339:15–19). This narrow range of susceptibilities is typical for HIV isolates from subjects of all ages and at all stages of HIV infection. Isolates of HIV from patients who receive AZT, however, chronically display progressive reductions of susceptibility to AZT over periods of months to years. Diminished susceptibility to AZT of an isolate of HIV-2 from a patient on prolonged therapy has also been reported (Pepin et al. Eighth International Conference on AIDS, Amsterdam, The Netherlands, Jul. 19–24, 1992 Abstract PoA 24401).

In addition to AZT, HIV resistance have been seen with other nucleosides and to nonnucleoside anti-retroviral drugs. For example, isolates resistant to AZT display diminished susceptibility to other nucleosides containing a 3'-azido moiety, including 3'-azido-2',3'-dideoxyuridine, 3'-azido-2', 'dideoxyguanosine, and 3'-azido-2',3'-dideoxyadenosine (Larder et al. (1989), supra; Larder et al. Antimicrob Agents Chemother (1990) 34:436–441). Additionally, AZT-resistant isolates are reported to display cross-resistance to didehydrodideoxythymidine (Rooke et al. Antimicrob. Agents Chemother. (1991) 35:988–991).

Drug resistance in HIV isolates is not limited to inhibitors of reverse transcriptase and virtually all drug targets for anti-HIV therapy are susceptible to the development of resistance. For example, a mutant with resistance to a protease inhibitor has been isolated that exhibits an eightfold reduction in susceptibility to a protease inhibitor (Patterson et al. Eighth International Conference on AIDS, Amsterdam, The Netherlands, Jul. 19–24, 1992, Abstract ThA 1506).

In the last five year, with the fast development of anti-HIV drugs and utilization of combination therapy, treatment of HIV infection with multiple antiviral drugs ("cocktails") have led to diminutions in the amount of viral RNA and virus detectable in blood by using current detection methods. It has been shown that combination therapy with 3 or more antiviral drugs, e.g. indinavir, zidovudine, and lamivudine, or alternatively, nevirapine, zidovudine, and didanosine, in previously untreated patients has resulted in profound decreases in viral burden (Wainberg, M. A. and Friedland, G. JAMA (1998) 279:1977–1983). It was believed that the combination antiviral regimens used must have blocked viral replication to the extent that the mutations that encode drug resistance could not occur. However, current studies showed that a growing number of patients are failing combination drug regimens (Deek, S. et al. the 5th Conference on Retroviruses and Opportunistic Infection, Chicago, Feb. 1–5, 1998, Abstract #419). Finding an effective salvage therapy for them is difficult.

In the clinical setting, drug resistance is often not detected until a patient manifests symptoms of disease progression, which is generally not observed until significantly after development of a drug resistant strain of virus. Thus, there is a clear need for an assay which can indicate the drug resistance of virus strains so drug therapy for a patient can be modified accordingly, and optimally as soon as resistance is detected rather than delaying until clinical symptoms are observed.

Currently the most commonly used assays for susceptibility of HIV to antiviral drugs involve the measurement of the inhibition of cytopathology, p24 production, or reverse transcriptase production of a laboratory strain of HIV in a lymphoblastoid cell line. Such assays may not be readily applied to clinical isolates of HIV. Examples of commonly used assays of drug susceptibility of clinical isolates have been the syncytial focus assay in CD4-HeLa cells (Chesebro, B. and Wehrly, K., J. Virol. (1988) 62:3779–3788), inhibition of p24 production in primary peripheral blood mononuclear cells, and reverse transcriptase (RT) assays using cultured primary T-cells from patient blood. (Richman et al. In: Current Protocols in Immunology, Coligan et al., eds, (1993) Brooklyn, J. Wiley).

One of the disadvantages associated with the syncytial focus assay is that it may only detect HIV viruses that exhibit a syncytial-inducing phenotype and that in practice may only be obtained from a minority of specimens from seropositive individuals. And the syncytial focus assays may not be used for screening for drugs that affect posttranslational processing, such as glycosidase and protease inhibitors. On the other hand, the p24 and RT assays may also suffer the limitations of difficult quantitation, low sensitivity and unproven clinical validity.

SUMMARY OF THE INVENTION

A recombinant cell is provided which comprises: a reporter sequence introduced into the recombinant cell comprising a reporter gene whose expression is regulated by a protein specific to HIV viruses which is expressed from a genome of an HIV virus upon infection of the recombinant cell by the HIV virus; the recombinant cell being capable of cell division and expressing a CD4 receptor and one or more additional cell surface receptors which facilitate productive infection of the recombinant cell by the HIV virus; and the recombinant cell enabling HIV virus which has infected the recombinant cell to replicate and infect non-infected cells in a culture of the recombinant cell.

As used herein, introducing a reporter sequence into a recombinant cell refers to the introduction of a sequence into cell by any of a variety of recombinant methodologies including, but not limited to, transformation, transfection and transduction.

The recombinant cell may optionally express a sufficient number of cell surface receptors to render the recombinant cell permissive to substantially all strains of HIV. Alternatively, the recombinant cell may express a selected group of cell surface receptors such that the recombinant cell is permissive to a selected group of strains of HIV. Examples of cell surface receptors which may be expressed by the recombinant cell include, but are not limited to CXCR4, CCR5, CCR1, CCR2b, CCR3, CCR4, CCR8, CXCR1, CXCR2, CXCR3, $CX_3CR1$, STRL33/BONZO and GPR15/BOB.

The stably transferred reporter sequence may optionally comprise a promoter sequence including an HIV virus specific enhancer sequence, and a reporter gene whose expression is regulated by binding of an HIV specific transactivator protein to the HIV specific enhancer sequence. According to this variation, the HIV specific transactivator protein is preferably Tat and the HIV specific enhancer sequence preferably comprises at least one copy of TAR sequence. Alternatively, the HIV specific protein may optionally regulates expression of the reporter sequence by a protein-protein interaction between the HIV specific protein and a transactivator protein present in the recombinant cell.

Examples of the HIV specific protein include, but are not limited to, HIV proteins Tat, Rev, Vpr, Vpx, Vif, Vpu, Nef, Gag, Env, RT, PR, and IN. The HIV specific protein may optionally be an HIV transactivator protein such as Tat.

Expression of the reporter gene in the recombinant cell may be is up-regulated or down-regulated by the HIV specific protein.

A method is provided for detecting a presence of HIV virus in a sample comprising: taking a culture of recombinant cells which (a) are capable of cell division, (b) express CD4 receptor and one or more additional cell surface receptors necessary to allow the HIV virus to infect, (c) enable the HIV virus to replicate and infect the noninfected cells in the cell culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus; contacting the cell culture with a sample to be analyzed for the presence of HIV virus in the sample; and detecting a change in a level of expression of the reporter gene in cells in the recombinant cell culture.

A method is also provided for detecting the presence of different strains of HIV virus in a sample comprising: taking a first culture of recombinant cells which (a) are capable of cell division, (b) express CD4 receptor and one or more additional cell surface receptors which render the first cell culture permissive to a first group of strains of HIV but does not render the first cell culture permissive to a second, different group of strains of HIV, (c) enable the HIV virus to replicate and infect the noninfected cells in the cell culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus; taking a second culture of recombinant cells which (a) are capable of cell division, (b) express CD4 receptor and one or more additional cell surface receptors which render the second culture permissive to the second group of strains of HIV but does not render the second cell culture permissive to the first group of strains of HIV, (c) enable the HIV virus to replicate and infect the noninfected cells in the cell culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus; contacting the first and second cell cultures with a sample to be analyzed for the presence of different strains of HIV virus; detecting a change in a level of expression of the reporter gene in cells in the first cell culture; detecting a change in a level of expression of the reporter gene in cells in the second cell culture; and distinguishing between the first and second groups of strains based on whether a change in a level of expression of the reporter gene occurs in the first or the second cell culture.

According to the above method, the first and second cultures of recombinant cells may optionally be mixed with each other. The reporter genes in the first and second cultures of recombinant cells may also optionally be different from each other so that cells of the first cell culture can be distinguished from cells of the second cell culture. This allows different strains of HIV virus to be detected in a single well containing cells from both cultures.

A method is also provided for detecting HIV drug resistance in a sample comprising: taking a culture of recombinant cells which (a) are capable of cell division, (b) express CD4 receptor and one or more additional cell surface receptors necessary to allow the HIV virus to infect, (c) enable the HIV virus to replicate and infect the noninfected cells in the cell culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus; contacting the cell culture with a sample containing HIV virus; adding one or more anti-HIV agents to the cell culture either before or after contacting the cell culture with the sample; and detecting a change in a level of expression of the reporter gene in the cells.

A method is also provided for taking a patient known to be infected with one or more strains of the HIV virus and determining what combination of one or more anti-HIV agents would be effective in treating the patient, the method comprising: taking a plurality of cell cultures, each of the cultures containing recombinant cells which (a) are capable of cell division, (b) express CD4 receptor and one or more additional cell surface receptors necessary to allow the HIV virus to infect, (c) enable the HIV virus to replicate and infect the noninfected cells in the cell culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus; contacting the cell cultures with a sample containing the HIV virus; adding a different set of one or more anti-HIV agents to each of the cell cultures, either before or after contacting the cell cultures with the sample; and comparing expression of the reporter gene in the plurality of cell cultures.

A method for screening compositions for anti-HIV activity comprising: taking a culture of recombinant cells which (a) are capable of cell division, (b) express CD4 receptor and one or more additional cell surface receptors necessary to allow the HIV virus to infect, (c) enable the HIV virus to replicate and infect the noninfected cells in the cell culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus; contacting the cell culture with a sample containing the HIV virus; adding one or more agents whose anti-HIV activity are unknown to the cell culture, either before or after contacting the cell cultures with the sample; and detecting a change in a level of expression of the reporter gene in the cells in the culture.

According to any one of the above methods, the recombinant cells in the cell cultures used in the methods may optionally comprise a reporter sequence introduced into the recombinant cells comprising a reporter gene whose expression is regulated by a protein specific to HIV viruses which is expressed from a genome of an HIV virus upon infection of the recombinant cell by the HIV virus; the recombinant cells being capable of cell division and expressing a CD4 receptor and one or more additional cell surface receptors which facilitate productive infection of the recombinant cell by the HIV virus; and the recombinant cells enabling the HIV virus which has infected the recombinant cell to replicate and infect non-infected cells in a culture of the recombinant cell.

Also according to any one of the above methods, the HIV specific protein may be any one of the HIV proteins Tat, Rev, Vpr, Vpx, Vif, Vpu, Nef, Gag, Env, RT, PR, and IN. The HIV specific protein may optionally be an HIV transactivator protein such as Tat.

Also according to any one of the above methods, the reporter sequence may comprise a promoter sequence including an HIV virus specific enhancer sequence, and a reporter gene whose expression is regulated by binding of an HIV specific transactivator protein to the HIV specific enhancer sequence. In one variation, the HIV specific transactivator protein is Tat and the HIV specific enhancer sequence comprises at least one copy of TAR sequence.

Also according to any one of the above methods, the one or more additional cell surface receptors expressed by the recombinant cell may include, but are not limited to CXCR4, CCR5, CCR1, CCR2b, CCR3, CCR4, CCR8, CXCR1, CXCR2, CXCR3, $CX_3CR1$, STRL33/BONZO and GPR15/BOB.

Also according to any one of the above methods, detecting a change in a level of expression of the reporter gene in the cells may include detecting a change in a level of expression of the reporter gene in individual cells.

Also according to any one of the above methods, detecting a change in a level of expression of the reporter gene in the cells may include detecting a change in a level of expression of the reporter gene across the cell culture.

Also according to any one of the above methods, detecting a change in a level of expression of the reporter gene in the cells may include detecting whether viral replication within the cell culture has occurred.

Also according to any one of the above methods, detecting a change in a level of expression of the reporter gene in the cells may include comparing a level of expression in cells contacted with the sample to a level of expression cells contacted with one or more control samples.

Also according to any one of the above methods, the sample may be any sample which might include HIV including, but not limited to whole blood, blood serum, isolated peripheral blood cells, T cells, and bone marrow.

Kits are also provided for performing the various methods of the present invention. These kits may include the cell line of the present invention and any two or more components used to perform these methods.

In one variation, a kit is provided which comprises: first and second recombinant cell lines, each recombinant cell line comprising: a reporter sequence introduced into the recombinant cells comprising a reporter gene whose expression is regulated by a protein specific to HIV viruses which is expressed from a genome of an HIV virus upon infection of the recombinant cell by the HIV virus, the recombinant cell line being capable of cell division and expressing a CD4 receptor and one or more additional cell surface receptors which facilitate productive infection of the recombinant cell by the HIV virus, and the recombinant cell line enabling the HIV virus which has infected the recombinant cell to replicate and infect non-infected cells in a culture of the recombinant cell; wherein the one or more additional cell surface receptors which the first recombinant cell line expresses renders the first recombinant cell line permissive to a first group of strains of HIV and the one or more additional cell surface receptors which the second recombinant cell line expresses renders the second recombinant cell line permissive to a second, different group of strains of HIV.

According to this variation, the first and second recombinant cell lines may optionally be mixed together in the kit. Also according to this variation, the first recombinant cell line may optionally include a first reporter gene and the second recombinant cell line may optionally include a second different reporter gene which allows the first and second recombinant cell lines to be independently identified.

DETAILED DESCRIPTION OF THE INVENTION

The present invention relates to new and useful methods including methods for detecting HIV, methods for detecting HIV drug resistance, methods for designing patient customized anti-HIV drug cocktail treatments, and methods for screening compositions for anti-HIV activity. Also provided are novel cell lines which may be used with the methods of the present invention.

The methods of the present invention use cells which (a) are capable of cell division; (b) are permissive to HIV virus; (c) express a reporter gene whose expression is selectively regulated by infection with HIV; and (d) allow viral replication of HIV in infected cells which enables cells within the same cell culture which are initially uninfected to become infected.

One of the advantages provided by the present invention is that the recombinant cells used are capable of cell division. As a result, it is easy to produce and maintain these cells for performing the various methods of the present invention.

A further advantage provided by the present invention is that the recombinant cells can be infected by multiple different strains of HIV, including wild-type and mutant HIV strains from clinical isolates or laboratory-adapted strains. As a result, the methods of the present invention have broad applicability to all strains of HIV.

Yet a further advantage provided by the present invention is that infection of the recombinant cells by an HIV virus can be easily monitored and measured. By using a reporter gene whose expression is regulated by infection with HIV, it is possible to detect HIV infection by simple detection methods, such as colorimetric methods. By expression of the reporter gene being selectively regulated by infection with HIV, false positive signals, for example due to infection by non-HIV viruses, are reduced.

A further advantage of the present invention is that the recombinant cells not only allow entry and infection of the HIV virus, but also facilitate efficient replication within the recombinant cell and transmission of the mature HIV virion to infect other cells in the culture. By using a cell line in which HIV is able to infect some cells in a cell culture, replicate, and then infect other cells in the cell culture, as well as by coupling viral replication with cell division, the signal produced by the reporter gene is amplified since more cells are infected than would be infected absent replication of HIV within the cell culture. For example, a single virion contained in a sample is ultimately able to infect all cells in the cell culture. This feature allows for sensitive detection of the HIV virus contained in a sample that is applied to the recombinant cell culture.

By exploiting the above-described advantages, as well as features further described in details below, the recombinant cell line can be used in a variety of methods or assays for many laboratory and clinical applications relating to HIV.

It should be noted that the methods and cells of the present invention can be modified and adapted for various viruses other than HIV, including but are not limited to retroviruses, coronaviruses, herpes viruses and adenoviruses. For example, an immortalized cell line can be constructed to comprise a panel of receptors and coreceptors to allow infection, replication and amplification of one or more strains of a target virus; and a reporter gene whose expression is regulated by a specific gene product expressed by the target virus.

1. Recombinant Cell Line

One aspect of the present invention relates to recombinant cells for use in detecting infection by an HIV virus. In one embodiment, the recombinant cell comprises:

a reporter sequence introduced into the recombinant cells comprising a reporter gene whose expression is regulated by a protein specific to HIV viruses which is expressed from a genome of an HIV virus upon infection of the recombinant cell by the HIV virus;

the recombinant cell being capable of cell division and expressing a CD4 receptor and one or more additional cell surface receptors which facilitate productive infection of the recombinant cell by the HIV virus; and the recombinant cell enabling the HIV virus which has infected the recombinant cell to replicate and infect non-infected cells in a culture of the recombinant cell.

Regulation of the reporter gene expression may involve up-regulation where the HIV specific protein causes expression of the reporter gene to begin or to increase. Alternatively, regulation of the reporter gene expression may involve down-regulation where the HIV specific protein causes expression of the reporter gene to cease or to decrease.

The HIV specific protein may be an HIV transactivator proteins such as Tat, an HIV regulatory protein such as Rev, HIV accessory proteins such as Vpr, Vpx, Vif, Vpu and Nef, HIV structural proteins such as Gag and Env, or HIV enzymatic proteins such as RT (reverse transcriptase), PR (protease) and IN (integrase). The regulation of the reporter sequence may be achieved by using various methods known in the art. For example expression of the reporter sequence can be regulated by direct binding of the transactivator protein Tat to an enhancer sequence upstream comprising at least one copy of TAR sequence. Alternatively, expression of the reporter gene can be regulated via protein-protein interaction between the HIV specific protein and an transactivator protein present in the recombinant cell.

In one variation of this embodiment, the reporter sequence in the recombinant cell comprises a promoter sequence including an HIV virus specific enhancer sequence, and a reporter gene whose expression is regulated by binding of an HIV specific transactivator protein to the HIV specific enhancer sequence.

According to this preferred embodiment, regulation of the reporter gene expression in the recombinant cells is achieved by using a promoter sequence including an HIV virus specific enhancer sequence which is transcriptionally responsive to an HIV specific transactivator protein. Upon infection by the HIV virus, the HIV specific transactivator protein expressed from the HIV genome binds to the HIV specific enhancer sequence and enhances expression of the reporter gene. The presence, absence or level of the reporter gene product is detected and used to indicate the infection of the HIV virus.

In a particularly preferred variation, the reporter sequence comprises at least one copy of TAR sequence as the HIV virus specific enhancer sequence. Expression of the reporter sequence is regulated by the binding of the HIV specific transactivator protein Tat to the enhancer sequence TAR.

a wide variety of reporter genes may be used in the present invention. Examples of proteins encoded by reporter genes include, but are not limited to, easily assayed enzymes such as β-galactosidase, luciferase, beta-glucuronidase, chloramphenicol acetyl transferase (CAT), secreted embryonic alkaline phosphatase (SEAP), fluorescent proteins such as green fluorescent protein (GFP), enhanced blue fluorescent protein (EBFP), enhanced yellow fluorescent protein (EYFP) and enhanced cyan fluorescent protein (ECFP); and proteins for which immunoassays are readily available such as hormones and cytokines. The expression of these reporter genes can also be monitored by measuring levels of mRNA transcribed from these genes.

The one or more additional cell surface receptors expressed by the recombinant cell may optionally include, but are not limited to, CXCR4, CCR5, other chemokine receptors such as CCR1, CCR2b, CCR3, CCR4, CCR8, CXCR1, CXCR2, CXCR3, $CX_3CR1$, and chemokine receptor-like orphan proteins such as STRL33/BONZO and GPR15/BOB.

The presence of CD4 and these one or more additional cell surface receptors allows efficient entry, infection and replication of HIV strains with different tropisms. By causing the recombinant cell to express as many cell surface receptors as possible, the recombinant cell may be rendered permissive to virtually all strains of HIV, regardless of tropism. This may be accomplished by transfecting or transducing the cell with all cell surface receptors known to be involved in HIV infection or by cell fusion with cells, such as T-cells or monocytes, which express these receptors on the cell surface. Alternatively, by causing the recombinant cell to express certain cell surface receptors or sets of cell surface receptors, it is possible to design the recombinant cell to be permissive to certain strains of HIV and to not be permissive to other strains of HIV. Thus, by selecting which cell surface receptors are expressed, cell lines can be designed for screening for particular strains or groups of strains of HIV virus.

The recombinant cell lines used in the present invention can be constructed from a wide variety of immortalized cell lines. In one embodiment, the recombinant cells are immortalized tumor cells. One of the advantages associated with using tumor cells is that tumor cells undergo relatively fast cell cycling or division, which may further enhance replication and amplification of the virus in the culture. The immortalized tumor cell lines can be generated from primary tumor cells or from established tumor cell lines. Alternatively, normal cells can also be used so long as the cells are immortalized. Examples include but are not limited to primary cells immortalized by transfection with telomerase gene and normal cells immortalized by SV40 tranformation. These immortalized cells can proliferate indefinitely, thus providing an ample and economic supply of cells.

Compared to human T-cells that have been used in the art for HIV virus it production, the recombinant cell lines of the present invention are relatively easier to culture, more stable, and less expensive. It has been acknowledged that the principle cell types targeted by HIV-1 are helper T-lymphocytes and cells of the monocyte macrophage lineage via the CD4 receptor pathway in vivo, while in tissue culture systems, HIV are cytopathic for $CD4^+$-lymphocytes and cause dysfunction of macrophages, which is directly accounted for depletion of T cells in the body. Since replicating HIV in infected individuals is readily detected in peripheral blood and lymph lodes, human peripheral mononuclear cells (PBMC), in particular, have been frequently used as host cells for HIV infection in vitro and anti-HIV drug-susceptibility testing. One of the disadvantages with PBMC cells is that these primary cells have to be obtained from donors, carefully cultured and freshly prepared each time. It is costly and inefficient to use these primary T-cells for commercial purposes. In addition, the permissiveness of these T-cells to different strains of HIV virus may vary with the donor, thus causing ambiguity in clinical testing. Thus, the recombinant cells of the present invention which can be produced in an ample supply, are permissive to HIV infection, relatively stable and can be cultured and manipulated more easily in vitro, are well suited for large scale commercial reproduction and use in high throughput screening.

2. Methods For Detecting HIV in a Sample

Methods are provided for detecting a presence of HIV virus in a sample. In one embodiment, the method comprises:

taking a culture of recombinant cells, which (a) are capable of cell division, (b) express CD4 receptor and one or more additional cell surface receptors necessary to allow the HIV virus to infect, (c) enable the HIV virus to replicate and infect the noninfected cells in the culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus;

contacting the cell culture with a sample to be analyzed for the presence of HIV virus in the sample; and detecting a change in a level of expression of the reporter gene in cells in the culture, such change being indicative of the HIV virus being present in the sample and infecting cells in the cell culture.

The culture of recombinant cells used in the method may be any cell culture which has the above described properties. The recombinant cells described in Section I are examples of cells having these properties and may be used in this method.

Detecting a change in a level of expression of the reporter gene in the cells in the culture may be performed by detecting a change in a level of expression of the reporter gene in individual cells or a change in a level of expression of the reporter gene across the cell culture.

In one embodiment, detecting a change in a level of expression includes detecting whether viral replication within the cell culture has occurred. Viral replication may be detected by detecting which cells are initially infected, and detecting a change in a level of expression of cells in the cell culture which were not initially infected.

In another embodiment, detecting a change in a level of expression includes comparing a level of expression in cells contacted with the sample to a level of expression cells contacted with one or more control samples. For example, cells contacted with a sample not containing HIV virus can serve as a negative control, while cells contacted with a sample containing HIV virus, recombinant and stabilized HIV virus, or another virus capable of infecting the cells and causing expression of the HIV specific protein, such as a modified adenovirus encoding Tat, can serve as a positive control. By using suitable controls, induction of the reporter gene expression may be better correlated with HIV infection.

It is noted that regulation of the reporter gene may be up regulation or down regulation. Accordingly, a change in the level of expression of the reporter gene may be an increase or decrease in reporter gene expression.

The methods described above can be used for diagnosis of HIV virus contained in variety of samples including, but are not limited to, whole blood, blood serum, isolated peripheral blood cells, T cells, other biological fluids such as urine, saliva, tears and semen, as well as isolated wild-type or mutant HIV viruses from laboratories or clinics. For example, whole blood of individuals can be tested for the presence of HIV virus by using the methods described above. In addition, blood or bone marrow samples from individual donors or samples from pooled blood stored in blood banks can be screened for the presence of HIV virus. The sensitivity of the methods to detect even a single HIV virion allows for the diagnosis of HIV in individuals at a very early stage of HIV infection and can be used to prevent HIV-positive blood from being transfused into patients.

One advantage of using the above-described method for HIV diagnosis is attributed to the specific response of the recombinant cells to HIV virus only. Because expression of the reporter gene is specifically regulated by HIV specific gene products, ambiguity in diagnosis or report of false positives can be avoided in the clinic. On the other hand, by using the above-described method, HIV virus may be detected in those individuals who are infected by HIV but do not have detectable levels of serum antibody (seronegatives), thereby reducing the incidents of false negatives which may arise from using antibody-based detection methods.

The methods described above can also be used to amplify HIV virus, especially strains with low occurrences in the blood sample and evasive to other detections. With the replication and amplification of the HIV virus in the recombinant cells, HIV virus with higher titer can be generated in the cell culture and isolated for further studies such as cloning of novel HIV strains.

The methods described above can also be used to differentiate strains or tropisms of HIV viruses in a sample by using recombinant cells selectively expressing certain HIV coreceptors. For example, CXCR4 coreceptor which is required by T-tropic strains can be selectively expressed in a first recombinant cell line to allow infection of T-tropic strains of HIV. Meanwhile, since M-tropic strains require CCR5 coreceptor to infect cells, a second recombinant cell line can be constructed to selectively express CCR5 to allow infection of M-tropic strains of HIV. By having the first and second recombinant cell lines expressing different coreceptors, the first and second recombinant cell lines can selectively detect T-tropic, M-tropic or dual-tropic strains in the presence of other strains of HIV virus.

Alternatively, the first recombinant cell line may include a first reporter gene such as GFP, while the second recombinant cell line may include a second reporter gene such as EBFP. When the first and second cell lines are mixed in one culture and contacted by a sample containing HIV virus with unknown tropism, selective expression of one reporter gene may indicate single tropism of the virus, while expression of both reporter genes may indicate dual tropism. Different fluorescences emitted by the first and second cell lines observed under microscope can facilitate independent identification of each cell line in one culture.

The methods described above can also be used for quantitative analysis of HIV virus in a sample. For example, by using control samples with varying titers, the viral load can be readily calculated by comparing to the control samples. Alternatively, the viral titer of a sample can also be determined by serially diluting the sample until end point infection is achieved in multiple cell culture plates, i.e. some of the cell culture plates are infected while the other plates are not infected by the diluted sample.

Methods for Detecting HIV Drug Resistance

Methods are also provided for detecting HIV drug resistance in a sample. These methods may be used to detect whether a course of treatment for HIV infection with one or more drugs is ineffective due to the presence of one or more strains of HIV which are resistant to the one or more drugs being used. These methods may also be used to isolate HIV strains which are resistant to one or more anti-HIV agents.

In one embodiment, the method comprises:

taking a culture of recombinant cells, which (a) are capable of cell division, (b) express CD4 receptor and one or more additional cell surface receptors necessary to allow the HIV virus to infect, (c) enable the HIV virus to replicate and infect the noninfected cells in the culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus;

contacting the cell culture with a sample containing HIV virus;

adding one or more anti-HIV agents to the cell culture either before or after contacting the cell culture with the sample; and detecting a change in a level of expression of the reporter gene in the cells.

Anti-HIV agents used in the methods may be any agents with known anti-HIV activities, either tested preclinically or clinically. Examples of anti-HIV agents which may be used to screen for HIV drug resistance include, but are not limited to, nucleoside HIV RT inhibitors such as ZIDOVUDINE, DIDANOSINE, ZALCITABINE, LAMIVUDINE, STAVUDINE, ABACAVIR, nonnucleoside RT inhibitors such as NEVIRAPINE, DELAVIRDINE, EFAVIRENZ, protease inhibitors such as INDINAVIR, RITONAVIR, SAQINAVIR, NELFINAVIR, AMPRENAVIR, and combinations thereof.

The culture of recombinant cells used in the method may be any cell which has the above described properties. The recombinant cells described in Section I are examples of cells having these properties and may be used in this method.

Detecting a change in a level of expression of the reporter gene in the cells in the culture may be performed by detecting a change in a level of expression of the reporter gene in individual cells or a change in a level of expression of the reporter gene across the cell culture.

In one embodiment, detecting a change in a level of expression includes detecting whether viral replication within the cell culture has occurred. Viral replication may be detected by detecting which cells are initially infected, and detecting a change in a level of expression of cells in the cell culture which were not initially infected.

In another embodiment, detecting a change in a level of expression includes comparing a level of expression in cells contacted with the sample to a level of expression cells contacted with one or more control samples. For example, cells contacted with a sample containing HIV virus but not with the one or more anti-HIV agents can serve as a negative control, while cells contacted with a sample containing a HIV virus that is not known to be resistant to the one or more anti-HIV agents added may preferably serve as a positive control. By using suitable controls, induction of the reporter gene expression may be better correlated with the resistance of the HIV virus to the agents.

It is noted that regulation of the reporter gene may be up regulation or down regulation. Accordingly, a change in the level of expression of the reporter gene may be an increase or decrease in reporter gene expression.

In one variation of this embodiment, the cell culture is contacted with one or more anti-HIV drugs before being contacted with a sample containing the HIV virus. Alternatively, the cell culture may be contacted with one or more anti-HIV drugs after being contacted with a sample containing the HIV virus and incubating for a time sufficient for the HIV virus replication to occur. This may be particularly advantageous for the initial amplification of the HIV virus with low titer in the sample before being tested for drug resistance.

The methods described above can be used to detect drug resistance of HIV virus contained in patient samples, isolated virus stocks or laboratory-adapted HIV strains. Owing to ultra sensitivity of the recombinant cells to a single HIV virion, the strains of HIV virus that escape the drug regimen or the ones that are not predominant circulating variants can replicate in the cell culture and be isolated for further genotypical analysis.

In comparison, the methods that have been used to detect anti-HIV drug resistance are less sensitive, time-consuming and technically demanding. The currently used methods include genotypic assays for detecting HIV genome mutation based on PCR amplification of the viral RNA followed by sequencing of the amplified DNA templates, and phenotypic assays based on recombinant HIV virus (Hirsch, M. S. (1998) JAMA 279:1964–1991). While the most sensitive PCR-based assay that has been developed may not be sensitive enough to detect plasma HIV RNA below 50 copies/mL, false positivity for mutations may be generated due to carry over from other HIV samples in the laboratory or from random polymerase errors during PCR. The recombinant virus assay requires a first RT-PCR amplification of plasma HIV RNA at more than 1000 copies/mL, cloning the viral cDNA into an HIV vector, and then growing up the virus in permissive cell line. The whole process may take more than two weeks to generate results and demand for highly skilled personnel to perform the test.

Thus, the methods provided in the present invention are more sensitive for detecting replicating HIV virus (at only about 5 virions/mL), more efficient for testing for HIV drug resistance (less than a week), and more economic for high throughput screening.

Methods for Designing Patient Customized HIV Cocktail Treatments

Methods are also provided for taking a patient known to be infected with one or more strains of the HIV virus and determining what combination of one or more anti-HIV agents will be effective in treating the patient. These methods can be used when a patient is initially being treated with anti-HIV agents or after a patient has been treated for a period of time with one or more anti-HIV agents and one or more resistant strains may have developed resistance to the anti-HIV agents being used.

In one embodiment, the method comprises:

taking a plurality of cell cultures, each of the cultures containing recombinant cells (a) are capable of cell division, (b) express CD4 receptor and one or more additional cell surface receptors necessary to allow the HIV virus to infect, (c) enable the HIV virus to replicate and infect the noninfected cells in the culture, and (d) comprises a reporter sequence introduced into the recombinant cells comprising a reporter gene whose expression is regulated by a protein specific to HIV viruses which is expressed from a genome of an HIV virus upon infection of the recombinant cell by the HIV virus;

contacting the cell cultures with a sample containing the HIV virus;

adding a different set of one or more anti-HIV agents to each of the cell cultures, either before or after contacting the cell cultures with the sample; and comparing expression of the reporter gene in the plurality of cell cultures.

In one variation, each cell culture of the plurality is contacted with a different set of one or more anti-HIV agents before being contacted with a sample containing the HIV virus.

In another variation, each cell culture of the plurality is contacted with a different set of one or more anti-HIV drugs after being contacted with a sample containing the HIV virus and incubating for a time sufficient for the HIV virus replication to occur.

The anti-HIV agents can be any agents with known anti-HIV activities, such as the ones described in Section 3, and combinations thereof.

The culture of recombinant cells used in the method may be any cell which has the above described properties. The recombinant cells described in Section I are examples of cell having these properties and may be used in this method.

Detecting a change in a level of expression of the reporter gene in the cells in the culture may be performed by detecting a change in a level of expression of the reporter gene in individual cells or a change in a level of expression of the reporter gene across the cell culture.

In one embodiment, detecting a change in a level of expression includes detecting whether viral replication within the cell culture has occurred. Viral replication may be detected by detecting which cells are initially infected, and detecting a change in a level of expression of cells in the cell culture which were not initially infected.

In yet another variation of this embodiment, the method further includes comparing the change in the level of expression of the reporter gene when different or no anti-HIV agents are used. For example, a recombinant cell culture that is contacted with the sample containing the HIV virus but not with the one or more anti-HIV agents can serve as a negative control, while a recombinant cell culture that is contacted with a sample containing HIV virus or a modified adenovirus, and the one or more anti-HIV agents can serve as a positive control. By using suitable controls, inhibition of the reporter gene expression may be better correlated with anti-HIV efficacy of the agents.

It is noted that regulation of the reporter gene may be up regulation or down regulation. Accordingly, a change in the level of expression of the reporter gene may be an increase or decrease in reporter gene expression.

In one variation of this embodiment, the cell culture is contacted with one or more anti-HIV agents before being contacted with a sample containing the HIV virus. Alternatively, the cell culture may be contacted with one or more anti-HIV agents after being contacted with a sample containing the HIV virus and incubating for a time sufficient for the HIV virus replication to occur. Such preamplification of the HIV virus may be advantageous for patient samples containing lower titer of the HIV virus to be tested against the anti-HIV agents.

The methods provided in this section can be used for screening an anti-HIV agent or agent combinations that are most active in inhibiting HIV viral infection and/or replication. The screening can be conducted against virtually all strains of HIV virus, regardless of their genotypes or tropisms. The results generated can help the physician of HIV infected patients monitor HIV drug resistance, optimize the drug regimen and use the most efficacious drug "cocktail" to treat the patient. By using such drug cocktails customized for each individual patient and adjusted during the course of the treatment, physicians may successfully prevent the HIV virus from developing drug resistance. Furthermore, physicians can avoid unnecessary side effects and drug toxicity that would otherwise arise from treating a patient with ineffective anti-HIV agents.

The ample and stable supply of the recombinant cells used in these methods, as well as the ease of culturing the cells, enables one to use the methods provided in this section in a high throughput screening format to test many more drug cocktail combinations than would otherwise have been possible. Furthermore, because the HIV virus contained in the sample from a patient may potentially harbor drug resistances strains, conventional drug screening may not have been effective in finding the optimum drug regimen. By using the methods provided in this section, the most efficacious drug regimen may be readily identified by designing and testing exhaustive combinations of different drugs that target different components of the HIV virus or HIV receptors.

5. Methods for Screening Compositions for Anti-HIV Activity

The present invention also relates to methods for screening compositions which are not known to have anti-HIV activity for anti-HIV activity. As used herein, a composition is intended to refer to any composition of matter, including single molecules, macromolecules such as proteins and nucleotides, or combinations of two or more molecules or macromolecules.

In one embodiment, the method comprises:
taking a culture of recombinant cells, which (a) are capable of cell division, (b) express CD4 receptor and one or more additional cell surface receptors necessary to allow the HIV virus to infect, (c) enable the HIV virus to replicate and infect the noninfected cells in the culture, and (d) comprise a reporter sequence introduced into the recombinant cells comprising a reporter gene whose expression is regulated by a protein specific to HIV viruses which is expressed from a genome of an HIV virus upon infection of the recombinant cell by the HIV virus;
contacting the cell culture with a sample containing the HIV virus;
adding one or more agents whose anti-HIV activity are unknown to the cell culture either before or after contacting the cell cultures with the sample; and
detecting a change in a level of expression of the reporter gene in the cells in the culture.

The culture of recombinant cells used in the method may be any cell culture which has the above described properties. The recombinant cells described in Section I are examples of cells having these properties and may be used in this method.

The agents can be any anti-HIV drug candidates from natural sources or synthetically generated. The agents can be any agent targeting any components of the HIV virus, such as RT inhibitors, protease inhibitors, antisense and ribozyme oligonucleotides against HIV mRNA or viral RNA genome, decoys of TAR sequence or RRE (rev response element), competitive inhibitors like soluble CD4, Gag or Env protein mutants, and agents that bind to HIV receptor or coreceptors and block the entry of HIV into the host cells.

Detecting a change in a level of expression of the reporter gene in the cells in the culture may be performed by detecting a change in a level of expression of the reporter gene in individual cells or a change in a level of expression of the reporter gene across the cell culture.

In one embodiment, detecting a change in a level of expression includes detecting whether viral replication within the cell culture has occurred. Viral replication may be detected by detecting which cells are initially infected, and detecting a change in a level of expression of cells in the cell culture which were not initially infected.

In another embodiment, detecting a change in a level of expression includes comparing a level of expression in a sample to a level of expression in one or more control samples. For example, a recombinant cell culture that is contacted with a sample containing HIV virus but not with any potentially anti-HIV agents can serve as a negative control, while a recombinant cell culture that is contacted with a sample containing an HIV virus and the one or more agents that are known to have anti-HIV activity can serve as a positive control. By using suitable controls, regulation of the reporter gene expression may be better correlated with anti-HIV efficacy of the agents.

It is noted that regulation of the reporter gene may be up regulation or down regulation. Accordingly, a change in the level of expression of the reporter gene may be an increase or decrease in reporter gene expression.

In one variation of this embodiment, the cell culture is contacted with one or more agents before being contacted with a sample containing the HIV virus. Alternatively, the cell culture may be contacted with one or more agents after being contacted with a sample containing the HIV virus and incubating for a time sufficient for the HIV virus replication to occur. This may be particularly advantageous for the initial amplification of the HIV virus with low titer in the sample before being tested against the agents.

The methods described above can be used for high throughput screening for anti-HIV drug candidates against various HIV containing samples, especially for libraries of compounds generated by combinatorial chemistry. These methods may be performed in any format that allows rapid preparation and processing of cells contained in multiple-well plates, such as 96-well plates. Stock solutions of the test agent as well as other assay reagents may be prepared manually and all subsequent pipetting, diluting, mixing, washing, incubating, sample readout and data collecting may be done using commercially available robotic pipetting equipment, automated work stations, analytical instruments for detecting the signal generated by the assay. Examples of such detectors include, but are not limited to, spectrophotometers, calorimeters, luminometers, fluorometers, and devices that measure the decay of radio-isotopes.

The methods described above are particularly cost-effective for use in high throughput screening because the recombinant cells are immortalized, easy to culture and more stable, compared to primary human cells such as PBMC cells. Furthermore, effects of multiple agents at multiple doses on HIV infection and replication can be directly monitored by detecting levels of reporter gene products in the 96-cell culture plates on a colorimetric or fluorescence plate reader.

6. Constructing a Recombinant Cell Line According to the Present Invention

The recombinant cells used in the present invention are immortalized cells. Human tumor cell lines are preferably used. Other transformed normal cells, such as human transformed primary embryonal kidney 293 cells, and human primary cells immortalized by transfection with telomerase (Bodnar, A.G. et al. (1998) Science 279:349–352) can also be used.

In order to create a cell line which is permissive to HIV infection, CD4 and one or more other HIV receptors are transfected, transduced or otherwise introduced into the immortalized cells. The one or more other HIV receptors preferably include CXCR4 and CCR5 receptors.

CD4 receptor is believed to be the primary receptor for HIV entry into the host cell. It has recently been discovered that specific chemokine receptors such as CXCR4 and CCR5 receptors play important roles in mediating HIV entry and tropism for different target cells (reviewed by Berger, E. a. (1997) AIDS 11, Suppl. a: S3-S16; Dimitrov, D. S. (1997) Cell 91: 721–730). Macrophages-tropic (M-tropic) strains of HIV virus can replicate in primary $CD4^+$ T cells and macrophages and use the beta-chemokine receptor CCR5 and less often, CCR3 receptor. T cell line-tropic (T-tropic) HIV strains can also replicate in primary $CD4^+$ T cells but can in addition infect established $CD4^+$ T cell lines in vitro via the alpha-chemokine receptor CXCR4. Many of the T-tropic strains can use CCR5 in addition to CXCR4. Chemokine receptor-like HIV coreceptor STRL33 is expressed in activated peripheral blood lymphocytes and T-cell lines and can function as an entry cofactor for Env proteins from M-tropic, T-tropic and dual tropic strains of HIV-1 and SIV. Other HIV coreceptors have also been identified by numerous in vitro assays, including chemokine receptors CCR2b, CCR3, CCR8 and CX3CR1 as well as several chemokine receptor-like orphan receptor proteins such as GPR15/BOB and STRL33/BONZO. Each or a set of these HIV coreceptors can mediate entry of different strains of HIV virus into the host cell. By transfecting, transducing or otherwise introducing these receptors into the immortalized cell line, the host cell line can be rendered permissive to HIV strains with broad-spectrum tropisms. In particular, by cell-cell fusion of the immortalized cell with cells expressing cell surface receptors known to be involved in HIV infection such as T-cells or monocytes, the immortalized cell can be transduced with various HIV receptors simultaneously.

By transfecting, transducing or otherwise introducing a selected set of coreceptors into an immortalized cell line or selectively expressing certain coreceptors on the cell surface, a cell line can be designed which is permissive to certain strains of HIV and is not be permissive to other strains of HIV. For example, CXCR4 coreceptor which is required by T-tropic strains can be selectively expressed in the recombinant cells to allow infection of T-tropic strains of HIV. Meanwhile, M-tropic strains require CCR5 coreceptor to infect cells. By having the recombinant cells not express CCR5 coreceptor, the recombinant cell line can selectively detect T-tropic strains in the presence of M-tropic strains.

In order to detect HIV infection with a high level of sensitivity, a "molecular switch" with high induction ratio is introduced into the immortalized cell line expressing CD4 receptor and the one or more additional HIV receptors. The molecular switch comprises a reporter gene whose expression is induced when the cells are infected by HIV. Various reporter genes can be used including lacZ (encoding β-galactosidase), luciferases gene, CAT gene, SEAP gene, and genes encoding fluorescent proteins such as green fluorescent protein (GFP), enhanced blue fluorescent protein (EBFP), enhanced yellow fluorescent protein (EYFP) and enhanced cyan fluorescent protein (ECFP).

The promoter region for the reporter gene contains a basic promoter and a single or multiple copies of HIV specific enhancer sequence. The basic promoter can be any cellular or viral basic promoters such as the basic promoter regions of β-actin promoter, insulin promoter, human cytomegalovirus (CMV) promoter, HIV-LTR (HIV-long terminal repeat), Rous sarcoma virus RSV-LTR, and simian virus SV40 promoter. The HIV specific enhancer sequence can be any sequence that can regulate the expression of the reporter gene via direct or indirect interaction with one or more HIV specific gene products. For example, the responsive element (TAR) for HIV transactivator protein Tat can be used to enhance the expression of the reporter gene. Upon infection of HIV, Tat expressed from the viral genome binds to TAR sequence and, coupled with the basic promoter, induces expression of the reporter gene. More than one copy of TAR sequence can be linked to further enhance expression of the reporter gene and raise the induction ratios.

Alternatively, expression of the reporter gene can be induced by protein-protein interactions between an HIV gene product, a DNA-binding protein (e.g. GAL4 DNA binding domain), a transactivator protein (e.g. VP16 transactivator domain derived from herpes simplex virus) that are expressed by the host cell. Upon binding of the HIV specific gene product to the DNA binding protein as well as to the transactivator protein, reconstitution of a transcription factor is achieved by bringing the DNA-binding protein and the transactivator protein into close approximately. The reconstituted transcription factor can then activate downstream reporter gene expression via the specific binding between the enhancer sequence (e.g. GAL4 enhancer sequence) upstream of the basic promoter with the DNA binding protein.

It should be noted that expression of a reporter gene can also be indirectly regulated by an HIV specific protein. For example, transcription of the reporter gene can be under the control a strong promoter, such as the bacteriophage T7 or SP6 promoters, while expression of T7 or SP6 polymerase is regulated by a promoter comprising a basic promoter and an HIV specific enhancer sequence. Upon binding of the HIV specific protein to the enhancer sequence, expression of T7 or SP6 polymerase is enhanced. As a result, T7 or SP6 polymerase expressed in the cell can then bind to the T7 or SP6 promoter upstream of the reporter gene and induce expression of the reporter gene in the cell.

Various methods can be used to introduce genes into the immortalized cells. Examples of methods that may be used include, but are not limited to, calcium phosphate-mediated direction transfection, liposome-assisted transfection, and virus-mediated transfection. HIV receptors can also be introduced into the host cell through cell fusion with natural cells expressing these receptors on the cell surface. Clones of cells expressing the transfected genes may be selected by antibiotics such as hygromyin, G418, zeocin, etc., or based on herpes simplex virus tk gene. Expression of each receptor gene may be confirmed by Western blot to detect the protein with an antibody, Northern blot to detect the RNA with a nucleotide probe, or by FACS using the HIV receptor expressed on the cell surface as antigens.

Two examples of plasmid vectors containing HIV receptor genes and a reporter gene are diagramed in FIG. 1A and 1B.

Figure 1:
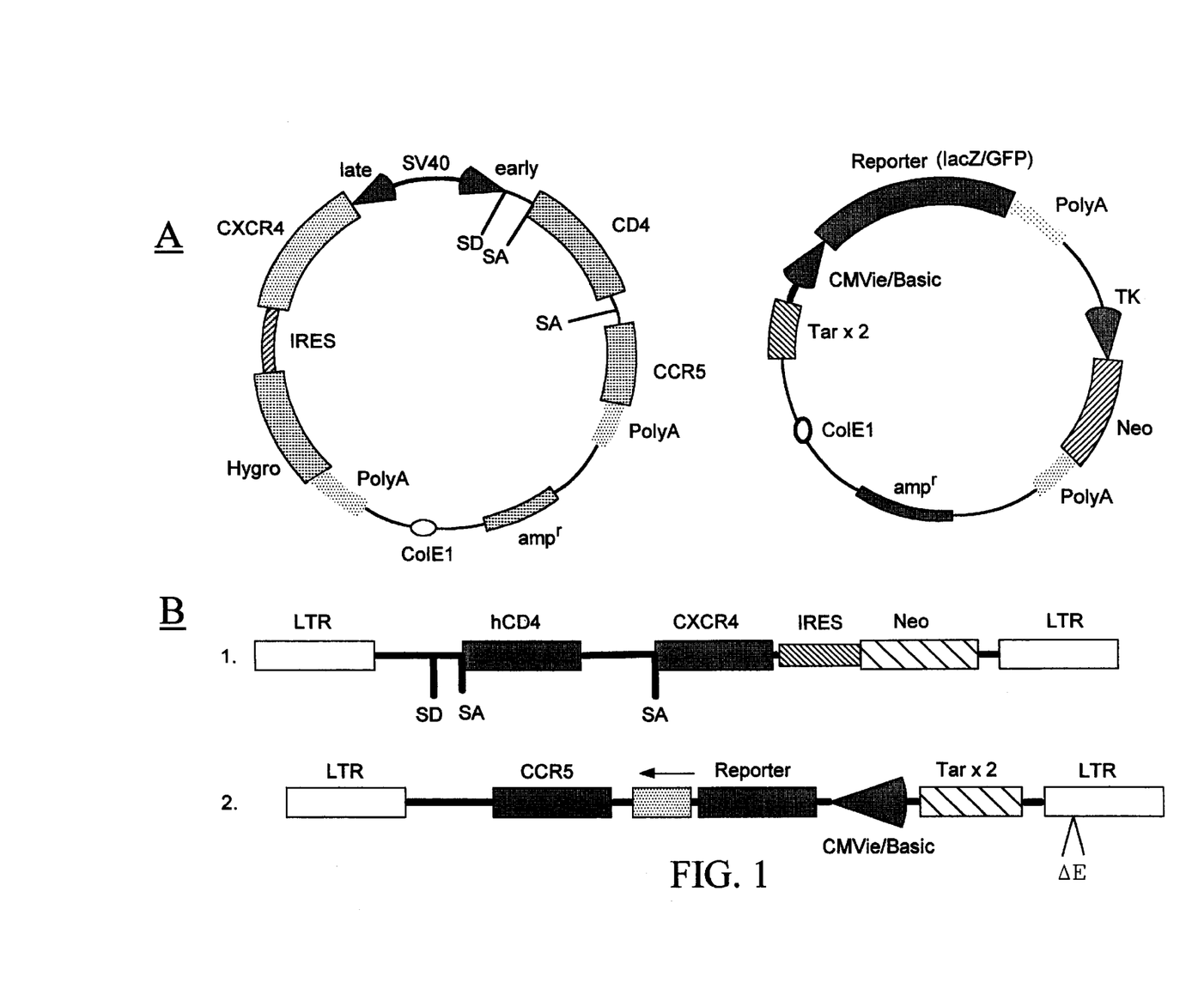
FIG. 1A illustrates expression plasmids for HIV receptors and a reporter gene.
FIG. 1B illustrates retroviral vectors for HIV receptors and a reporter gene.

As illustrated in FIG. 1, CD4 and HIV co-receptors are expressed from SV40 early and late promoters in opposite directions. Genes encoding CD4 and CCR5 receptors are expressed from SV40 early promoter by a splicing mechanism at the SA sites. Genes encoding CXCR4 and hygromycin fin resistance are expressed bicistronically from SV40 late promoter with Hygro being separated by an internal ribosome entry site (IRES). Expression of hygromycin resistance gene enables selection of the cell. The plasmid also contains prokaryotic replication origin and ampicillin-resistance gene for DNA propagation in bacteria. The reporter gene is carried by a separate plasmid that contains a second selection gene (tk). The two plasmids may be co-transfected into HeLa cells simultaneously or sequentially. Cell clones expressing all of the transfected genes can be selected with antibiotics accordingly.

Genes encoding HIV receptor and coreceptors may also be expressed from the two retroviral vectors illustrated in FIG. 1B. The receptors gene are expressed from the murine leukemia virus (MLV) LTR-promoter, each protein is expressed from a spliced mRNA or from an IRES (B. 1). The reporter sequence is carried by a second retroviral vector. Transcription of the reporter gene is in the opposite direction of the MLV LTR promoter with the enhancer sequence deleted in order to prevent unregulated expression from the LTR promoter (B.2).

These vectors are packaged into infectious but replication-incompetent virions by using a packaging cell line, such as those stable or transient production lines based on the 293T cell line. The packaging cell line expresses all the necessary proteins, Gag, Pol and Env, that are required for packaging, processing, reverse transcription, and integration of recombinant retroviral genome containing the Psi packaging signal.

The retroviral vectors are transfected into the packaging cell line. The virions produced in the packaging cells are then collected and used to infect a target cell. Since the virons are replication-incompetent, the genes carried by the retroviral vectors are stably integrated into the target cell genome and can be expressed under the control of the upstream promoter without producing infectious virions. The cells expressing all of the transduced genes can be selected with antibiotics and confirmed by Northern, Western blots or FACS accordingly. Alternatively, the cells expressing the reporter sequence can be selected by infecting the cell culture with a modified adenovirus carrying HIV specific gene such as tat. D It should be noted that expression of HIV receptors can also be controlled by an inducible promoter such as a tetracycline responsive element TRE. For example, one or more of the HIV coreceptors can be selectively presented on the cell surface by a controlled expression using the Tet-on and Tet-off expression systems provided by Clontech (Gossen, M. and Bujard, H. (1992) Proc. Natl. Acad. Sci. USA 89: 5547–5551). In the Tet-on system, gene expression is activated by the addition of a tetracycline derivative doxycycline (Dox), whereas in the Tet-off system, gene expression is turned on by the withdrawn of tetracyline (To) or Dox. Any other inducible mammalian gene expression systems may also be used. Examples include systems using heat shock factors, steroid hormones, heavy metal ions, phorbol ester and interferons to conditionally expressing genes in mammalian cells.

Overall, the present invention provides novel recombinant cell lines and methods using these cell lines. These methods are convenient, cost-effective and ultra sensitive for the detection of HIV infection and replication. These methods can be very useful for high throughput screening in preclinical drug discovery and development, as well as designing more efficacious anti-HIV drug cocktails in the clinic to combat HIV drug resistance.

EXAMPLE

1. Productive Infection of Recombinant HeLa Cells with HIV virus

Figure 2:
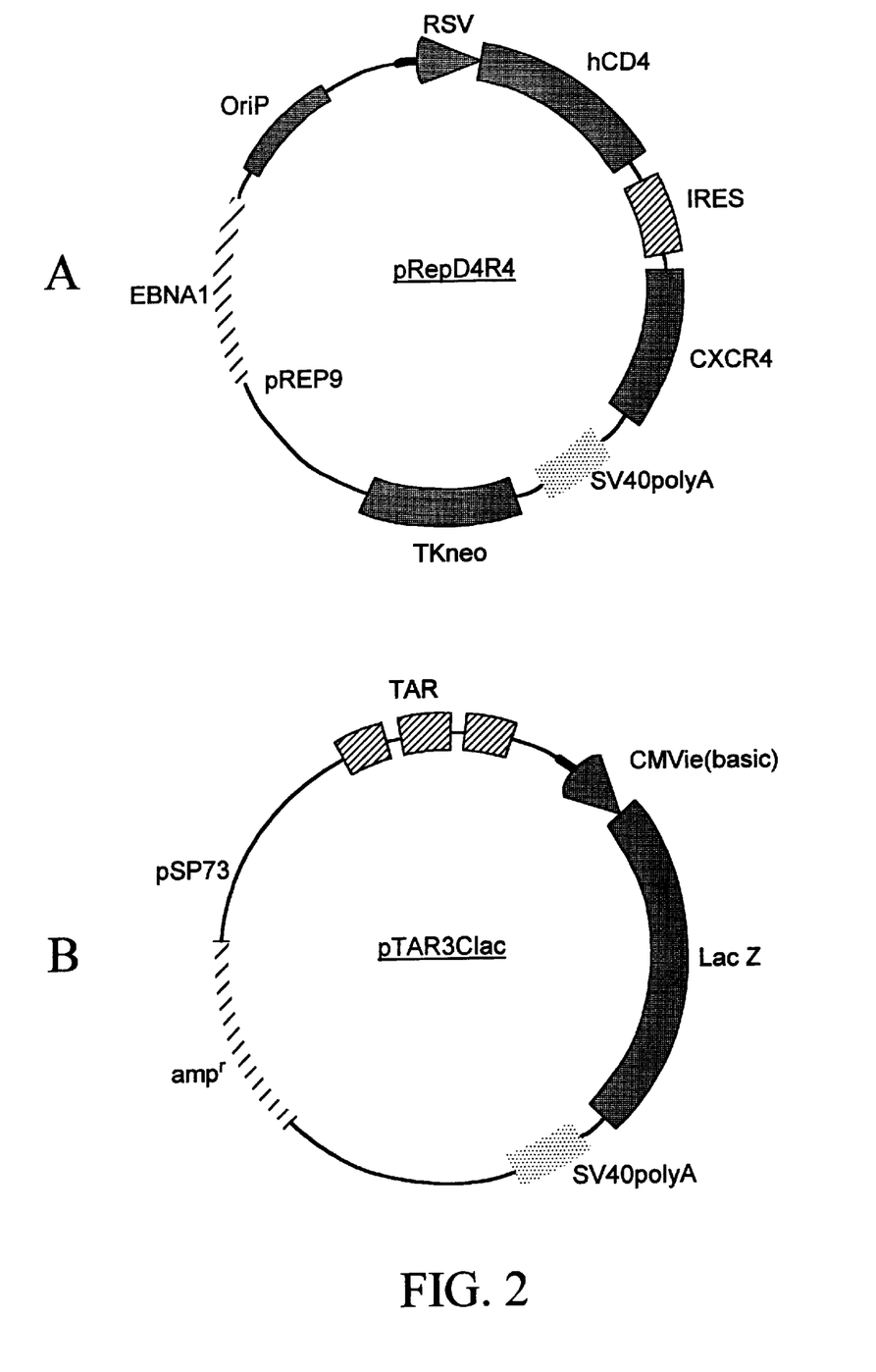
FIG. 2A illustrates an expression plasmid for human CD4 and CXCR4 receptors.
FIG. 2B illustrates a plasmid for a lacZ reporter gene.

A recombinant cell line was established from human cervical cancer HeLa cells. The HeLa cells were cotransfected with an expression vector (pRepD4R4) and a vector (pTAR3Clac) at a 1:1 ratio. As shown in FIG. 2A the expression vector pRepD4R4 includes CD4 receptor and CXCR4 receptor genes that are separated by an IRES sequence. As shown FIG. 2B the vector pTAR3Clac includes a reporter sequence comprising a promoter region that includes three copies of TAR sequences and a CMV basic promoter, and a lacZ reporter gene whose expression is under the control of the promoter. The stably-transfected cells were selected by culturing in medium containing G418 at 900 μg/ml. Each clone of the cells selected was subsequently cultured in duplicates, and one of the duplicates was infected with a low titer HIV stock solution. The low-titer HIV stock was collected from supernatant of a HeLa cell culture that was transfected with a B-cell tropic HIV provirus DNA (strain GRCSF) and incubated for 3 days post transfection.

Upon infection of HIV contained in the stock solution, Tat protein expressed from the viral genome binds to TAR and induces expression of lacZ reporter gene to produce high level of β-galactosidase. The cell clones expressing β-galactosidase and stained blue with X-gal were identified, and the cells from the uninfected duplicate of the darkest blue colony were propagated. Such selected cells were designated as HeLaD4R4 cells.

HeLaD4R4 cells constructed as described above were tested for HIV infection. HeLaT4 cells (also called HT4) which express human CD4 receptor were used as a control. The HeLaD4R4 cells and HeLaT4 cells were grown up in DMEM and 5% bovine calf serum.

Exponentially growing cells were cultured in a six-well plate and infected with 1 ml of a diluted HIV stock (about 10 infectious particles/ml) obtained from HIV provirus transfected HeLa cell culture as described above. The cells were continuously cultured, and fixed with 1% formaldehyde for 2 minutes 1, 3, 4, 5 days after the initial infection. The cells were fixed with 0.5% formaldehyde for 2 min. and stained with X-gal (0.5%) at 37° C. over night. Since the lacZ reporter gene product, β-galactosidase, converts the substrate from colorless to dark blue, cells expressing β-galactosidase as a result of being infected with HIV appear distinctly blue.

FIG. 3A shows the control HeLaT4 cells after three days of being exposed to HIV. As can be seen, almost all of the HeLa cells were not stained blue, with few cell stained faint blue. This indicates that cells without HIV CXCR4 were poorly infected and the HIV virus did not replicate within the cell culture.

FIGS. 3B–2E shows HeLaD4R4 after 1, 3, 4, and 5 days. As can be seen in FIG. 3B, infection can be readily detected after 1 day, as shown by the blue cells. As can be seen in FIGS. 3C and 3D respectively, progressively more cells were infected and stained blue after 3 and 4 days. As can be seen in FIG. 3E, virtually all cells in the well were infected and stained dark blue after 5 days.

The results shown in FIGS. 3B–3E indicate that following initial infection of a few cells by about ten HIV virions, HIV was able to undergo a productive infection, i.e. an infection of a cell which is fully permissive for virus replication and production of progeny virions (Stevenson, M. AIDS 11 Suppl. a: S25–33). In addition, the infected cells appear to retain normal morphology, i.e. remaining attached to the substrate of the culture plate instead of rounding up and detaching from the plate.

The results shown in FIG. 3E are particularly significant because HIV virions initially added to the sample were able to replicate within the cell culture and spread to infect other cells that are not infected originally (compare FIGS. 3B and 3E). This is in significant contrast to an increase of cells stained blue simply due to cell division.

FIG. 3F illustrates a further experiment where AZT (100 μg/ml) was added to inhibit HIV replication and infection. As can be seen in FIG. 3F, after four days of incubation in the presence of AZT only a few clusters of cells were infected and stained blue. The sparse clusters of blue cells are most likely cells divided from the few cells that were initially infected by the HIV virions added to the well.

Figure 3:
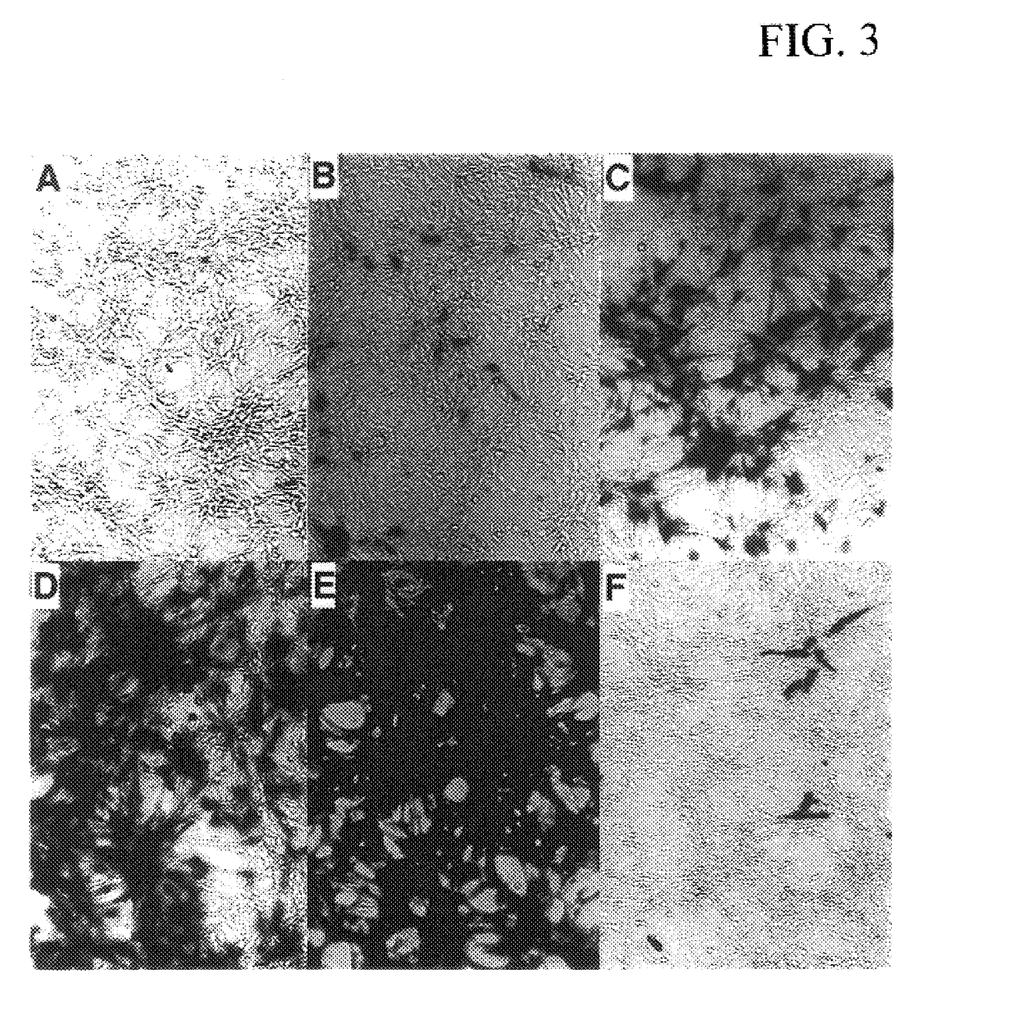
FIG. 3A shows HeLaT4 cells cultured in the presence of HIV virus and later processed with X-Gal.
FIG. 3B shows HeLa D4R4 cells cultured in the presence of HIV virus and later processed with X-Gal 1 day after the initial infection.
FIG. 3C shows HeLa D4R4 cells cultured in the presence of HIV virus and later processed with X-Gal 3 days after the initial infection.
FIG. 3D shows HeLa D4R4 cells cultured in the presence of HIV virus and later processed with X-Gal 4 days after the initial infection.
FIG. 3E shows HeLa D4R4 cells cultured in the presence of HIV virus and later processed with X-Gal 5 days after the initial infection.
FIG. 3F shows HeLa D4R4 cells cultured in the presence of HIV virus and AZT and later processed with X-Gal.

By comparing FIG. 2F to FIGS. 3B–3E, one can see that AZT was effective as an anti-HIV agent since the expression of the reporter gene was significantly reduced due to the presence of AZT. This comparison of the results in FIG. 3F to FIGS. 3B–3E is an example of how the present invention can be used to detect HIV drug resistance and to screen compositions for anti-HIV activity.

2. Method for HIV Diagnosis

An example is provided for detecting HIV in a sample. This method can be used to diagnose a patient infected with HIV. According to the method, recombinant cells are seeded into a multiple well plate. a small amount of serum from an individual to be tested is added to duplicates of the wells. After two to four days incubation, the cells are processed and the results are analyzed depending on the type of reporter gene used. For example, when lacZ gene is used as the reporter gene for the recombinant cells, the cells are treated with a processing solution containing the substrate X-Gal for β-galactosidase, low concentration of formaldehyde (1 %) and glutaraldehyde (the 0.1%) to gently fix the cells while not inactivating the reporter protein. When a green fluorescent protein (GFP) gene is as the reporter gene for the recombinant cells, the cells are observed under an UV microscope directly. The presence of cells emitting green fluorescence indicate that the cells may have been infected by HIV virus contained in the sample. By using GFP as a reporter gene replication of HIV can be directed monitored any time during the incubation without fixing and processing cells to ensure that enough HIV virus has been replicated within the culture.

The above-described diagnosis test can be used as an independent test for HIV infected patients, or in conjunction with HIV drug resistance and other HIV diagnosis tests.

a positive control agent may be used to ensure that the recombinant cells are responsive to HIV infection. a defective common cold virus strain carrying an HIV tat gene that encodes HIV transactivator protein Tat may be used as a positive control agent. The common cold virus is used as a vector to transfer the HIV tat gene into cells to mimic HIV infection. HIV itself may not be ideal for use as a positive control because HIV may not be sufficient stable and can easily lose its activity, thus the virus may not be stored for an extended period of time. In contrast, the common cold virus can be dried into powder and stored for a long time. In addition, this strains of common cold virus is derived from a strain of common cold virus (adenovirus type 5) that is defective in viral replication, therefore safer for an extensive usage as a it positive control.

3. Method for Detecting HIV Drug Resistance

An example of how to perform the method for detecting HIV drug resistance is provided. Recombinant cells are seeded into each well of a multiple-well plate. Duplicate wells contain each anti-HIV agent to be tested. a small amount of patient serum is added to each well and incubated for a few days. After two to four days of incubation, the cells are processed and the results are analyzed depending on the type of reporter gene used. For example, when lacZ gene is used as the reporter gene for the recombinant cells, the cells are treated with a processing solution containing the substrate X-Gal for β-galactosidase, low concentration of formaldehyde (1 %) and glutaraldehyde the (0.1 %) to gently fix the cells while not inactivating the reporter protein. For quantitative analysis, levels of beta-Gal can be measured by an ONPG assay on the cell extract. When a green fluorescent protein (GFP) gene is used as the reporter gene for the recombinant cells, the cells are observed under an UV microscope directly. For quantitative analysis, the fluorescent cells are sorted by FACS and numbers of cells expressing the GFP reporter are measured.

If the cells in the wells containing a particular drug express the reporter gene at a sufficient level, it indicates that the HIV virus contained in the sample may be resistant to the drug at the tested dose, and the virus has replicated and spread the infection among the recombinant cells in the presence of the anti-HIV drug.

Wells where no serum sample has been added can be used as a negative control. Negative controls can be performed for each agent being tested. a positive control, for example using the positive control agent described in Example 2 (adenovirus carrying HIV tat gene), can also be performed for each agent tested to ensure that the recombinant cells function properly.

4. Method for Determining Viral Load in a Patient Serum

An example of how to perform the method for determining viral load in patient serum is provided. About 1 milliliter of patient's serum is diluted progressively, such as 1:10, 1:100, 1:1000, etc, and added to wells containing the recombinant cells. The highest dilution that still induces expression of the reporter gene of the recombinant cells in the well is the titer (concentration) of the HIV in the patient serum. When the viral load become low, finer steps of dilution may be performed to determine more accurately the numbers of viral particles in the patient's serum.

The method can be used to determine how many viral particles per milliliter are present in patient serum. Since the recombinant cells in a culture are sensitive to infection of even a single virion, this method can detect infection by only one viral particle, therefore suitable for detecting a patient sample containing low titer HIV, even a few viral particles per milliliter of patient serum. Such a high sensitivity is important for monitoring the progress of anti-HIV drug treatment. Compared to the "ultra-sensitive" PCR-based assays that can only detect hundreds or more viral particles per milliliter of patient serum, this method is more sensitive and can be used to detect much lower titer HIV in the sample. This is particularly important for detecting HIV virus in a patient sample after anti-HIV drug treatment when viral titer is below the detectable level of conventional HIV detection methods.

5. Method for Screening for Anti-HIV Agents

Described here is an example of a method for performing high throughput anti-HIV drug screening. To screen for new anti-HIV agents, the recombinant cells are seeded into a multiple well plate, such as 96-well plate. To each well the agent to be tested for anti-HIV activity is added. a small amount of HIV stock is added to each well, so that the cells in each well are so; infected with about 10 viral particles. After a few days of incubation, the cells in the wells are analyzed on a colorimetric or fluorescence plate reader. The wells are compared with one or more wells containing the recombinant cell and virus but not the agent. Inhibition of the expression of the reporter gene in wells containing an agent indicates that the agent may have anti-HIV activity at the tested dose. Once potential anti-HIV agents have been identified, the test may be repeated to further confirm the anti-HIV activity of the agent.

Throughout this application, various publications are referenced. The disclosures of these publications, and the references cited therein, in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

What is claimed is:

1. A recombinant cell comprising:
    a reporter sequence comprising a reporter gene whose expression is regulated by a protein specific to HIV; and
    a heterologous sequence which encodes CD4 and one or more additional cell surface receptors,
        wherein the heterologous sequence expresses CD4 and the one or more additional cell surface receptors at elevated levels as compared to the cell In the absence of expression by the heterologous sequence such that productive infection of the recombinant cell by the HIV is achieved, which is defined by HIV viral replication and the infection of non-infected cells in a culture of the recombinant cell.

2. The recombinant cell according to claim 1 wherein reporter gene expression is up-regulated by the HIV specific protein.

3. The recombinant cell according to claim 1 wherein the HIV specific protein is an HIV transactivator protein.

4. The recombinant cell according to claim 4 wherein the HIV transactivator protein is Tat.

5. The recombinant cell according to claim 1 wherein the reporter sequence comprises
    a promoter
    an HIV virus specific enhancer sequence, and
    a reporter gene whose expression is regulated by binding of an HIV specific transactivator protein to the HIV specific enhancer sequence.

6. The recombinant cell according to claim 5 wherein the HIV specific transactivator protein is Tat and the HIV specific enhancer sequence comprises at least one copy of TAR sequence.

7. The recombinant cell according to claim 1 wherein the HIV specific protein regulates expression of the reporter sequence by a protein-protein interaction between the HIV specific protein and a transactivator protein present in the recombinant cell.

8. The recombinant cell according to claim 1 wherein the reporter gene is selected from the group consisting of β-galactosidase, luciferase, beta-glucuronidase, chloramphenicol acetyl transferase (CAT), secreted embryonic alkaline phosphatase (SEAP), hormones and cytokines.

9. The recombinant cell according to claim 1 wherein the one or more additional cell surface receptors expressed by the recombinant cell are selected from the group consisting of CXCR4, CCR5, CCR1, CCR2b, CCR3, CCR4, CCR8, CXCR1, CXCR2, CXCR3, $CX_3CR1$, STRL33/BONZO and GPR15/BOB.

10. The recombinant cell according to claim 1 wherein the one or more additional cell surface receptors expressed by the recombinant cell comprises CXCR4.

11. The recombinant cell according to claim 1 wherein the one or more additional cell surface receptors expressed by the recombinant cell comprises CCR5.

12. The recombinant cell according to claim 1 wherein the one or more additional cell surface receptors expressed by the recombinant cell comprises CXCR4 and CCR1.

13. The recombinant cell according to claim 1 wherein the recombinant cell expresses a sufficient number of cell surface receptors to render the recombinant cell permissive to substantially all strains of HIV.

14. The recombinant cell according to claim 1 wherein the recombinant cell is a tumor cell.

15. The recombinant cell according to claim 1 wherein the recombinant cell is a cell which has been immortalized by introducing a gene into the cell which renders the cell line immortalized.

16. The recombinant cell of claim 1, wherein the recombinant cell is capable of achieving productive infection of a clinically isolated HIV.

17. The recombinant cell of claim 1, wherein the CD4 receptor and the one or more additional cell surface receptors are expressed by an adenoviral vector tranduced into the recombinant cell.

18. A recombinant cell comprising:
a reporter sequence comprising a reporter gene whose expression is regulated by Tat protein of HIV; and
a heterologous sequence which encodes CD4, CXCR4 and COR5,
wherein the heterologous sequence expresses CD4, CXCR4 and CCR5 at elevated levels as compared to the cell In the absence of expression by the heterologous sequence such that productive infection of the recombinant cell by the HIV is achieved, which is defined by HIV viral replication and the infection of non-infected cells in a culture of the recombinant cell.

19. The recombinant cell of claim 18, wherein the recombinant cell is capable of achieving productive infection of a clinically isolated HIV.

20. A recombinant cell comprising:
a reporter sequence comprising
a promoter sequence,
an enhancer sequence comprising at least two copies of an HIV TAR sequence, and
a reporter gene whose expression Is regulated by Tat protein of HIV through binding of the Tat protein to the TAR sequence of the enhancer sequence; wherein
the recombinant cell is capable of cell division and genetically modified to express CD4 and one or more additional cell surface receptors at elevated levels relative to a non-genetically modified form of the recombinant cell such that productive infection of the recombinant cell by the HIV virus is achieved, which is defined by HIV viral replication and the infection of non-infected cells in a culture of the recombinant cell.

21. The recombinant cell of claim 20, wherein the recombinant cell is capable of facilitating productive infection of a clinically isolated HIV.

22. The recombinant cell of claim 61, wherein the one or more additional cell surface receptors are CXCR4 and CCR5.

23. The recombinant cell of claim 20, wherein the promoter is selected from the basic promoter region of the promoter selected from the group consisting of Mactin promoter, insulin promoter, human cytomegalovirus promoter, Rous sarcoma virus promoter, and simian virus SV40 promoter.

24. The recombinant cell of claim 20, wherein the promoter is an early promoter of human cytomegalovirus.

* * * * *